(12) United States Patent
Tison et al.

(10) Patent No.: US 11,199,476 B2
(45) Date of Patent: Dec. 14, 2021

(54) DISSOLVABLE NANOFIBER MATERIALS AND SPECIMEN RECOVERY KITS INCLUDING THE SAME FOR HIGH EFFICIENCY SPECIMEN RECOVERY

(71) Applicant: LUNA INNOVATIONS INCORPORATED, Roanoke, VA (US)

(72) Inventors: Christopher K. Tison, Roanoke, VA (US); Blaine Butler, Roanoke, VA (US); Matthew Patterson, Roanoke, VA (US); Nikolai Braun, Roanoke, VA (US)

(73) Assignee: LUNA INNOVATIONS INCORPORATED, Roanoke, VA (US)

( * ) Notice: Subject to any disclaimer, the term of this patent is extended or adjusted under 35 U.S.C. 154(b) by 0 days.

(21) Appl. No.: 16/470,668

(22) PCT Filed: Dec. 21, 2017

(86) PCT No.: PCT/US2017/067882
§ 371 (c)(1),
(2) Date: Jun. 18, 2019

(87) PCT Pub. No.: WO2018/132244
PCT Pub. Date: Jul. 19, 2018

(65) Prior Publication Data
US 2020/0088607 A1    Mar. 19, 2020

Related U.S. Application Data

(60) Provisional application No. 62/445,868, filed on Jan. 13, 2017.

(51) Int. Cl.
| | | |
|---|---|---|
| *G01N 1/02* | (2006.01) |
| *C12Q 1/24* | (2006.01) |
| *C12Q 1/6806* | (2018.01) |
| *G01N 1/40* | (2006.01) |

(52) U.S. Cl.
CPC ............. *G01N 1/02* (2013.01); *C12Q 1/24* (2013.01); *C12Q 1/6806* (2013.01); *G01N 1/4055* (2013.01); *G01N 2001/028* (2013.01)

(58) Field of Classification Search
None
See application file for complete search history.

(56) References Cited

U.S. PATENT DOCUMENTS

| | | |
|---|---|---|
| 9,480,966 B2 | 11/2016 | Kovacs et al. |
| 2003/0073830 A1 | 4/2003 | Heath et al. |
| 2003/0152974 A1 | 8/2003 | Gauch et al. |
| 2005/0288616 A1 | 12/2005 | Bozenbury, Jr. et al. |
| 2007/0244314 A1 | 10/2007 | Mori |
| 2011/0008771 A1 | 1/2011 | Hanselle et al. |
| 2011/0250256 A1 | 10/2011 | Hyun-Oh et al. |
| 2012/0045752 A1 | 2/2012 | Ensor et al. |
| 2015/0031035 A1 | 1/2015 | Kvam et al. |

FOREIGN PATENT DOCUMENTS

| | | |
|---|---|---|
| TW | 1376440 | 11/2012 |
| WO | WO 2013/123500 | 8/2013 |

OTHER PUBLICATIONS

Buffer AVL, "Material Safety Data Sheet", QIAGEN GmbH, Feb. 27, 2013. [retrieved from the internet on Feb. 4, 2017], http://www.qiagen.com/data/Support/MSDS/US/Buffer_AVL_US6.pdf, 5 pages.
International Search Report for PCT/US2017/067882 dated Feb. 21, 2018, 2 pages.
Communication—Supplementary European Search Report, EP Application No. 17891572.4, dated Aug. 13, 2020.

*Primary Examiner* — Robert S Cabral
(74) *Attorney, Agent, or Firm* — Nixon & Vanderhye P.C.

(57) ABSTRACT

Biological specimen recovery materials include cellulose acetate nanofibers that are capable of dissolution upon contact with a liquid comprising a dissolution effective amount (e.g., between about 1 to about 10M) guanidinium isothiocyanate (GITC). Kits containing the materials (e.g., in the form of a swab, filtration media or surface wipe) and a dissolution liquid containing the dissolution effective amount of guanidinium isothiocyanate (GITC) are also provided.

10 Claims, 4 Drawing Sheets

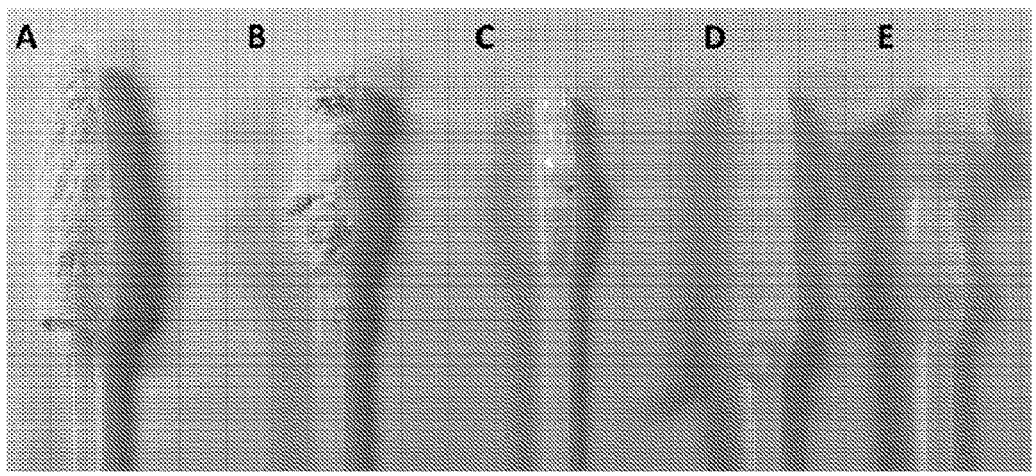
FIG. 3 (Comparative): Cellulose acetate swabs: (A) As-produced control, (B) DMF/EMIMAcO 1 minute, (C) DMF/EMIMAcO 5 minute, (D) DMSO/EMIMAcO 1 minute, and (E) DMSO/EMIMAcO 5 minute.
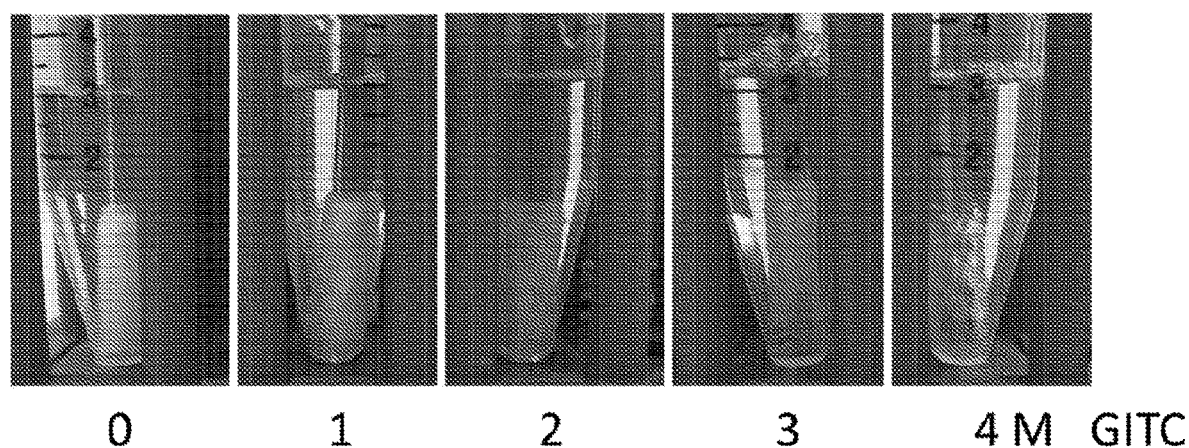
FIG. 4 (Invention): Dissolution of cellulose acetate nanofiber swab material in varying concentration of GITC in DI water. Images taken after 3 minutes immersion with no agitation

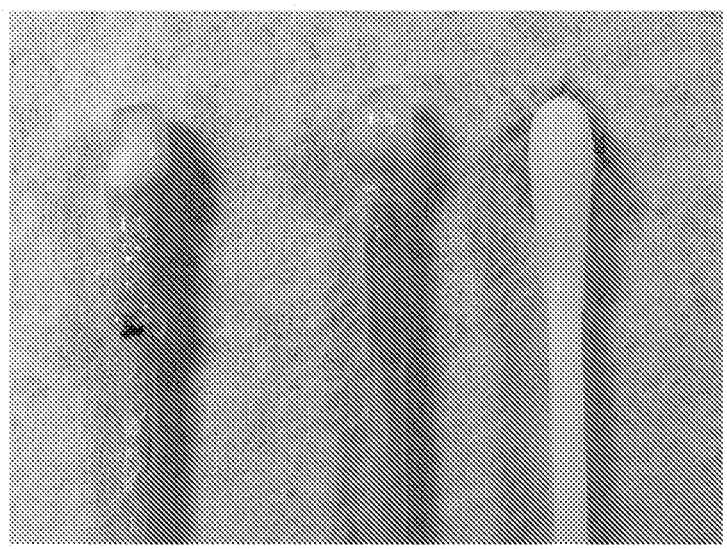
FIG. 5: Swabs following immersion in Multi-Sample DNA Lysis Buffer (swabs of invention appear one the left and center with a standard cotton swab appearing on the right).

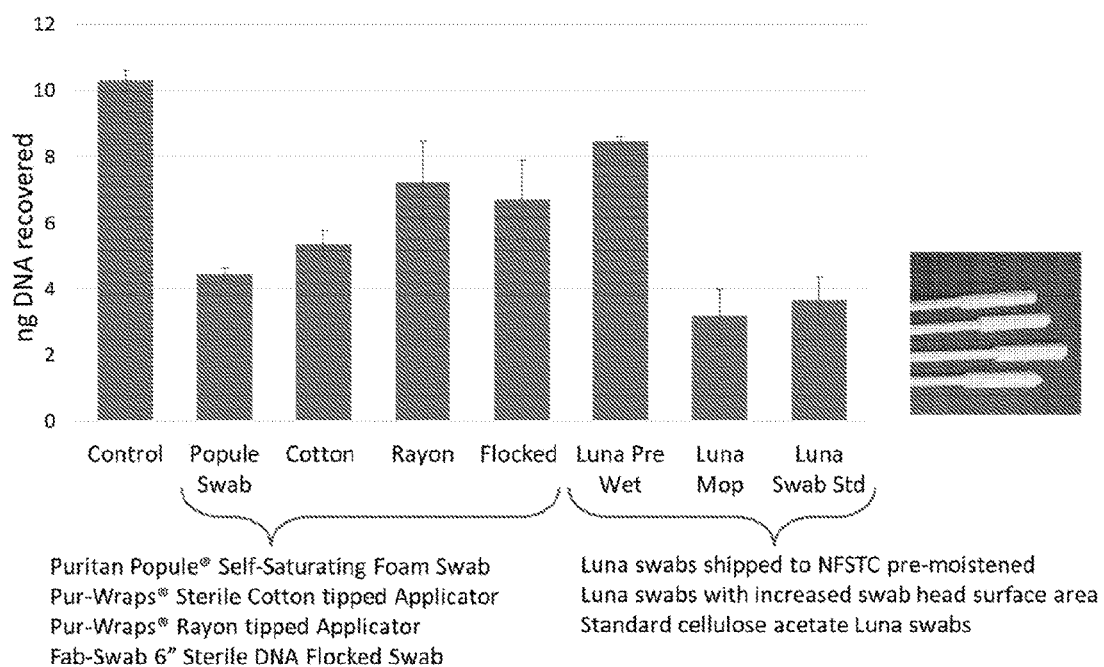
FIG. 6: Recovery of DNA (20 µL blood sample, Qiagen EZ1 automated system with supplied buffers from the Qiagen QIAmp DNA Investigator Kit) from a variety of commercially available swabs and Luna swabs. This recovery does not include dissolution, but instead demonstrates optimal performance in a forensic situation where pre-wetting of the swab is desired.

DISSOLVABLE NANOFIBER MATERIALS AND SPECIMEN RECOVERY KITS INCLUDING THE SAME FOR HIGH EFFICIENCY SPECIMEN RECOVERY

CROSS-REFERENCE TO RELATED APPLICATION

This application is the U.S. national phase of International Application No. PCT/US2017/067882 filed Dec. 21, 2017 which designated the U.S. and claims priority to U.S. Provisional Application No. 62/445,868 filed Jan. 13, 2017, the entire contents of each of which are hereby incorporated by reference.

GOVERNMENT RIGHTS

This invention was made with Government support under Defense Advanced Research Projects Agency (DARPA) No. D14PC0010 and US Army—Army Research Office (USAARO) Contract Nos. W911NF-15-P-0070 and W911NF-16-C-0113. The Government has certain rights to the invention.

FIELD

The disclosed embodiments herein relate generally to dissolvable cellulose acetate nanofiber materials that may advantageously be used for biological specimen recovery, e.g. kits comprised of a biological collector which includes the dissolvable cellulose acetate nanofiber materials, and a specimen recovery liquid upon contact by which the cellulose acetate nanofiber materials are dissolvable.

BACKGROUND AND SUMMARY

The emergence of new infectious diseases and the resurgence of diseases previously controlled by vaccination and treatment are creating unprecedented public health challenges, constituting a significant threat to both global health and national security. The movement of people and goods around the world has increased the opportunity for a local outbreak to become a world-wide pandemic before the causative agent(s) can be identified. Recent disease outbreaks of Sudden Acute Respiratory Syndrome (SARS), multidrug-resistant tuberculosis, Ebola viral hemorrhagic fever, West Nile viral encephalitis, intentional anthrax, and H5N1 viral infections in humans have heightened concerns about global health security. Significant resources have been invested in biosecurity, biosurveillance and medical countermeasures to mitigate these threats. The ability to rapidly detect and identify infectious organisms is critical for the accurate diagnosis of seasonal and sporadic outbreaks, emerging pathogens and agents of bioterrorism. The past fifteen years have seen significant technological advances in molecular diagnostics and the use of nucleic acid-based detection for pathogen identification. This has significantly expanded the range of pathogens that can be identified in clinical laboratories. Accurate detection requires high quality biological specimens, which are dependent on proper collection, transport, and storage.

One of the most critical aspects of accurate and sensitive detection is recovery of as much sample as possible for testing and sample identification. For blood draws, this means obtaining as large a volume as possible within reasonable timelines and pain thresholds. For specimens obtained using other means, however, tuning the capture material to the specimen is of critical importance. One of the most frequently used technologies for sample acquisition is a "swab" used for the capture of nasal or other bodily fluids for transfer to a diagnostic test. When sample specimens are collected, there is frequently lost sample during the recovery process. (Nasal discharge is being used as a representative sample for this document, but the same issues exist for nasopharyngeal swabbing, vaginal or rectal swabbing, or specimens such as blood, semen, saliva, or other biological samples either freshly deposited or dried onto virtually any surface.) Traditionally, swabs are agitated mechanically to recover sample, but proteins, nucleic acids, or enzymes needed for detection often bind irreversibly to the swab materials. Mechanical entrapment within the swab is also possible.

Additionally, capture materials can be used in the form of a filter that captures specimens for analysis from large volumes of liquid or gas phase materials that are passed through. This can be a passively set material where capture of specimen happens by simple diffusion, or it can use active pumping of gas or liquid over the material. Capture material can be used in systems where it is spooled on a tape, allowing analysis of capture over time, or on single stationary filters that are used to collect the total amount of material for a given time period of capture.

Capturing the largest sample possible during clinical, environmental, or forensic sampling and then recovering 100% of the captured specimen is critical to diagnosis of disease, identification of biological or chemical terror events or environmental catastrophe, and essential to successful forensic analysis. Existing swabs or filters used for sample acquisition suffer from either low liquid absorption and sample capture (flocked swabs) or low sample recovery (traditional wound cotton swabs). There exists a need to develop a material that can capture significant specimen and from which the captured sample can be easily, rapidly, and completely recovered without compromising the sample or subsequent analysis.

Diagnostics for non-blood-associated pathogens often use swabs as a specimen-collecting tool. For example, swabs are used to collect throat specimens for Group A *Streptococcus*, nasal and nasopharyngeal specimens for *Staphylococcus aureus*, influenza virus and respiratory syncytial virus (RSV), female endocervical or male urethral specimens for *Neisseria* gonorrhea and *Chlamydia trachomatis*, and fecal swabs for viral gastroenteritis. Swabs should have tip size/shape appropriate for the sampling site, and the swab tip material and microstructure should provide efficient sample capture and target recovery in the presence of sample matrix components (e.g., human cells, body fluids, and other contaminants). Commercially available swabs are currently utilized with a variety of swab tip materials (e.g., nylon, rayon, cotton, polyester, polyurethane, and alginate polymer) and microstructures/shapes (e.g., tightly wound, knitted, flocked fiber, and reticulated). In laboratory settings, swabs are typically agitated by vortex mixing to release biological material into a transfer fluid that is analyzed by culture, immunoassays (ELISA), or further purified to analyze nucleic acids (PCR). The following Table 1 provides a list of existing swab tip compositions and representative manufacturers and applications:

TABLE 1

Swab Tip Composition or Chemistry and Representative Manufacturers and Uses

| Chemistry/Composition | Manufacturer | Technology/Use Notes |
|---|---|---|
| Rayon | Copan Diagnostics | High-absorbent fiber |
| Cotton | Puritan Medical Products | High-absorbent fiber |
| Mid-turbinate flocked nylon | Copan Diagnostics | Low-absorbent fiber |
| Regular tip flocked nylon | Copan Diagnostics | Low-absorbent fiber |
| Polyester | Contec Inc | Low-absorbent knitted-pattern |
| Polyurethane | Foamtec | Low-absorbent foam |
| Calcium alginate | Puritan Medical Products | Dissolvable swab |

Low-absorbent systems (flocked, foam, knit-pattern) are typically designed to ensure that recovery of the sample is maximized. These swabs are designed to ensure that there is minimal entrapment or non-specific binding of the specimen to the swab, thereby enhancing recovery. Thus, these swab systems sacrifice capture efficiency for recovery.

High-absorbent systems, typically composed of tightly-wound fibers, are designed to ensure that specimen capture is maximized. These systems can absorb substantial volume, but suffer from low recovery (as low as 2-10%) due to irreversible non-specific binding and/or entrapment of bacteria, viruses, and cell debris within the swab tip.

Calcium alginate swabs are dissolvable in specific buffers, but result in very high viscosity liquid samples that are frequently incompatible with downstream processing.

What has been needed in the art therefore is a material that can ensure substantially complete capture of the desired specimen yet be easily dissolvable for analysis. It is towards fulfilling such needs that the embodiments disclosed herein are directed.

In general, the embodiments disclosed herein are in the form of a nanofiber material system that is capable of complete dissolution in a variety of controlled buffer solutions. The material is comprised of cellulose acetate that is electrospun into nanofibers having average diameters in the range of from about 20 to about 20000 nm, e.g., between about 100 to about 500 nm. Electrospinning is a technique through which non-woven polymer mats are prepared from a polymeric solution in a way that results in very small fibers. This small fiber diameter results in unique characteristics such as high surface area, high apparent porosity, and low total mass. Cellulose acetate is advantageous as a specimen collection material due to its relative low cost and ability to be dissolved in a variety of buffers.

These and other aspects of the present invention will become more clear after careful consideration is given to the following detailed description of a presently preferred exemplary embodiment thereof.

BRIEF DESCRIPTION OF THE DRAWINGS

Reference will be made to the accompanying drawings, wherein:

FIG. 3 is a photograph showing images of cellulose acetate swabs after contact with various ionic liquids;

FIG. 4 are photographs showing the dissolution of cellulose acetate nanofiber swab material in varying concentrations of guanidinium isothiocyanate (GITC) in deionized (DI) water taken after 3 minutes of immersion with no agitation;

FIG. 5 is a photograph showing the cellulose acetate nanofiber swabs (two left swabs) following immersion in multi-sample DNA lysis buffer in comparison to a standard cotton swab (right most swab); and FIG. 6 is a graphical presentation of the recovery of DNA (20 μl blood sample, Qiagen EZ1 automated system with supplied buffers from Qiagen QIAmp DNA Investigator Kit) for a number of commercially available swabs and the swabs of the current invention.

DETAILED DESCRIPTION

To address the need for materials with both high capture and high recovery, a cellulose acetate nanofiber swab or filter material that dissolves in a variety of liquids is provided by the embodiments disclosed herein. The swab or filter material is stable in traditional aqueous buffers containing salts, detergents or alcohols, and therefore there is no degradation or dissolution of the swab during typical sampling processes or routine environmental work. Complete dissolution of the material occurs however in less than 1 minute (with agitation) in a buffer with a dissolution effective amount of guanidinium isothiocyanate (GITC).

The embodiments of the material disclosed herein are especially useful as diagnostic (medical) swabs, forensic (sampling) swabs, sample "wipes," or as a filtration material. In certain preferred embodiments, materials for nasal or nasal pharyngeal sampling are provided, but other uses are envisioned. For example, swabs could be used to collect throat specimens, endocervical or male urethral specimens, and fecal specimens. Swabs could also be used to collect forensic specimens of biological samples, or chemical residues. Filter material could be used for environmental monitoring or targeted aerial particulate sifting. The various devices disclosed herein may include the dissolvable nanofiber materials in woven and/or nonwoven forms as may be required for the specific end use application.

The swab with the nanofiber material according to the embodiments disclosed herein is designed to be used according to standard practice for sample acquisition, where subsequent specimen recovery will occur in the desired swab dissolution buffer (which must necessarily comprise a dissolution effective amount of between about 1 to about 10M GITC, for example between about 3 to about 6M GITC or about 4M GITC). The dissolution buffer may be included in a kit containing the non-woven nanofiber capture material (e.g. in the form of a collection of swabs), or can be a buffer acquired separately by the end user. One example of a commercially available cell lysis buffer is that provided by the commonly used MagMAX™ PCR DNA and RNA isolation kits from Life Technologies which contain GITC. By selecting buffers that come with existing kits to induce dissolution of the swabs, the embodiments of the swabs according to the invention can be implemented with no needed changes to the processing of specimens. For filtration applications, the material can be envisioned as being held between filter membranes, or adhered/attached to support structure. It is also feasible that the material could be used for non-biological specimen collection and analysis. For example, trace metal analysis in water or gas flumes, etc.

In all applications (swabs/filters) the key of the system is ease of specimen capture and then dissolution of the nanofibers for complete specimen recovery.

A. Cellulose Acetate Nanofibers

Figure 1:
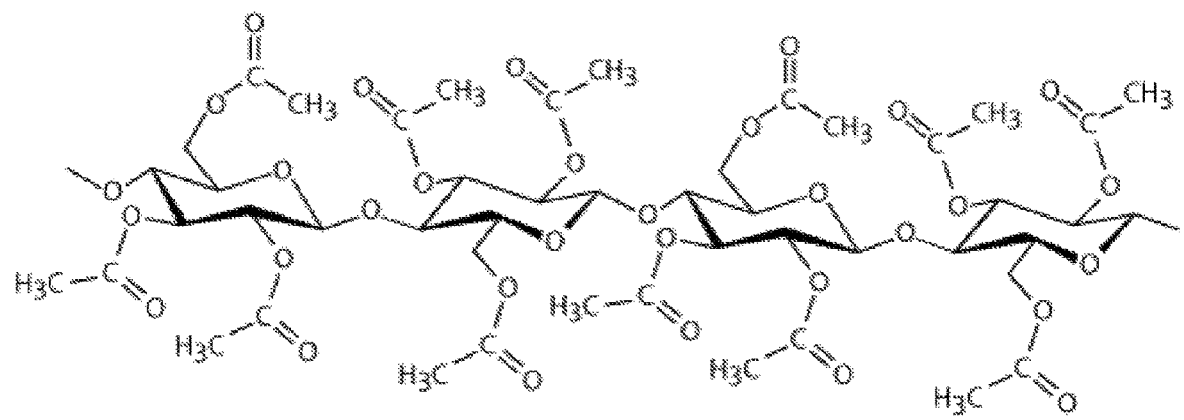
FIG. 1 is a chemical formula schematically depicting the structure of cellulose acetate with the acetated group being circled.

As noted above, the embodiments disclosed herein necessarily comprise a cellulose acetate (CA) nanofibers, for example, CA nanofibers in the form of a nonwoven mass and/or yarns and/or filaments of CA nanofibers woven together or with other non-CA yarns or fibers. As shown in FIG. 1, cellulose acetate is the preferred polymer to be employed in the non-woven nanofiber web materials disclosed herein and is the acetate ester of cellulose that is derived from cellulose by deconstructing wood pulp and reacting it with acetic acid and acetic anhydride in the presence of sulfuric acid. It is then put through a controlled, partial hydrolysis to remove the sulfate group and acetate groups. The most common CA fiber has on average less than one to three acetate groups per glucose. Solvents that are used to prepare CA nanofibers for the embodiments disclosed herein include chloroform, hexafluoroisopropanol (HFIP), acetone, acetyl acetone, toluene, carbinol, primary alcohols (e.g., methanol, ethanol, and propanol), dimethylacetamide (DMAC), dimethylformamide (DMF), dimethyl sulfoxide (DMSO), 1,3-dimethylamylamine (DMAA), tetrahydro furuan (THF), dichloro methane (DCM), dichloro ethane (DCE), diethyl ether, ethyl acetate, acetonitrile, acetic acid, hydrochloric acid, hydrofluoric acid and various mixtures of the same.

The weight average molecular weight (MW) of cellulose acetate that may be employed in the embodiments disclosed herein is between about 30,000 to about 300,000 g/mol. The cellulose acetate may also be employed at between about 5 to about 50% wt/vol, e.g., between about 10 to about 20% wt/vol in a solvent or solvent mixture as described previously in order to produce the non-woven nanofibers. One presently preferred cellulose acetate that may be employed satisfactorily to form the non-woven nanofiber collection materials described herein may have a degree of acetylation of between 25 and 50%, e.g., about 40%.

Both needle-based and needle-free electrospinning systems may satisfactorily be used for the production of cellulose acetate nanofibers to form the nanofiber materials for use in the swabs and filters as described herein. The method of production is not as critical provided that the resulting nanofiber diameter is between about 20 to about 2000 nm, for example between about 100 to about 500 nm) with a nonwoven mat thickness of between about 5 to about 5000 µm, e.g., between about 50 to about 500 µm.

The individual nanofibers may be continuous filaments of indefinite length. Alternatively (or additionally) embodiments of the devices herein may include staple fibers having a length between about 0.75 inches to about 7 inches, typically between about 3 inches to about 7 inches. In those embodiments whereby the devices include a fabric of woven nanofibers, the individual yarns may be multifilamentary yarns comprised of the continuous filaments and/or spun staple fibers. The particular weave pattern is not critical.

Traditional needle-based electrospinning relies on the forced ejection of a polymer solution from a highly charged syringe using a syringe pump. The flow of the polymer solution out of the needle tip results in the formation of a Taylor Cone as the charged polymer is traveling across a certain distance towards a grounded collection surface. Needle-free systems, such as the NanoSpider® electrospinning technology commercially available from Elmarco or a ball-based electrospinning system commercially available from Stellenbosch Nanofiber Company, may be used for the production of these fibers which relies on highly charged substrates that are coated with a thin film of the polymer of interest. When the voltage is high enough, forced ejection of the polymer solution occurs and dozens or hundreds of nanofibers are produced simultaneously. Those skilled in this art will appreciate that nanofibers suitable for use in the specimen recovery kits as disclosed herein can be produced by virtually any conventional fiber-forming method, such as self-assembly, spinneret extrusions, electrospraying or using other production technologies well known in the art.

It is commonly understood that cellulose acetate will inhibit DNA yield of silica column or functionalized magnetic bead-based DNA isolations. For this reason, it may be necessary to limit the quantity of cellulose acetate of the various biological collection devices described herein when used in a DNA extraction. Commercial DNA extraction kits with high GITC extraction buffers (e.g. ThermoFisher Prepfiler™ forensic DNA extraction kit, Qiagen® EZ1 DNA Investigator kit, Promega DNA IQ® system) are optimized to work with commonly encountered quantities of materials on which to perform DNA extractions.

By way of example, quantities of cellulose acetate that are permissible to include with standard commercial extraction protocols should not exceed 50 mg of cellulose acetate material, for example, a range of 1 mg to 50 mg of cellulose acetate material. When designing a biological sample collection device, the quantity of the material used in the entire device must be limited to not be greater than 50 mg of cellulose acetate, or the design should provide a method by which only a 50 mg or less subset of cellulose acetate of the collection device is used for the DNA extraction.

B. Buffer Solutions for Controlled Dissolution

It is important for the embodiments disclosed herein that fast and complete dissolution of the electrospun cellulose acetate fiber swabs be achieved in order to facilitate rapid release of all biological specimens (pathogens, proteins, etc.), trace metals or other analytes of interest in order to make them available for downstream detection. As high temperatures and long time periods are not compatible with biospecimen analysis, the dissolution buffer solutions must therefore be capable of dissolving the cellulose acetate nanofibers at a) moderate ambient temperature (e.g., room temperature of about 20° C.), b) with minimal agitation requirements, c) short time frames, and d) no degradation to the captured biospecimens or analytes. In order to achieve these requirements, it is necessary that controlled dissolution of the cellulose acetate nanofiber material be accomplished by contact with a solution containing a dissolution effective amount of guanidinium isothiocyanate (GITC), for example between 1 to 10M solution of GITC, typically between about 3 to about 6M GITC (e.g., about 4M GITC). Further, DNA extraction techniques used with cellulose acetate nanofiber-containing collection devices can be optimized to maximize the recovery of biological materials by increasing volumes, quantities and concentrations of liquid reagents used in the various DNA extraction methods.

The dissolution buffer may additionally comprise up to 99 wt. %, for example be present in an amount of less than 70 wt. %, typically between about 10 wt. % to about 70 wt. %, e.g., between about 30 wt. % to about 50 wt. %, of a primary alcohol, such as methanol, ethanol, propanol and the like. If a primary alcohol is employed in combination with GITC, then the concentration of GITC in the dissolution buffer may be reduced, e.g., to between about 1 to about 4M GITC.

Examples

The following materials using the following variables, may successfully be used to produce on a lab scale the nanofiber materials materials of the embodiments disclosed herein:

TABLE 2

Cellulose acetate nanofiber swab production variables

| Variable | Range/Description |
|---|---|
| Cellulose Acetate Molecular Weight | ~30-3000,000 g/mol (e.g., 30,000-~50,000 g/mol) |
| Cellulose Acetate Concentration | 5-50% (wt/vol), e.g., 10-20% (wt/vol) |
| Cellulose Acetate Degree of Acetylation (DA) | 20-50% acetylated |
| Solvent | 0-99 wt. % of any combination of chloroform, HFIP, acetone, acetyl acetone, toluene, carbinol, ethanol, methanol, propanol, DMAC, DMF, DMSO, DMAA, THD, THF, DCM, DCE, diethylether, ethyl acetate, acetonitrile acetic acid, HCl, HF, formic acid |
| Production Method | Needle-based electrospinning Needle-free electrospinning |
| Collection Method | Aluminum foil (2D) Ethanol Capture Bath (3D) Moving substrate (Needle-free system) Stationary substrate (Needle-free system) |

The method of production, the method of collecting the fibers, the solvent, and the concentration of CA utilized all have effects on the absorption and release rates of the swabs, as discussed below. The use of cellulose acetate is an important aspect of the embodiments disclosed herein because it allows a variety of low-cost synthesis methods and can allow rapid dissolution, as discussed below. Combining the chemistry (cellulose acetate) with the material morphology (nanofibers) provides the unique behavior required for efficient capture and recovery of specimens.

Figure 2:
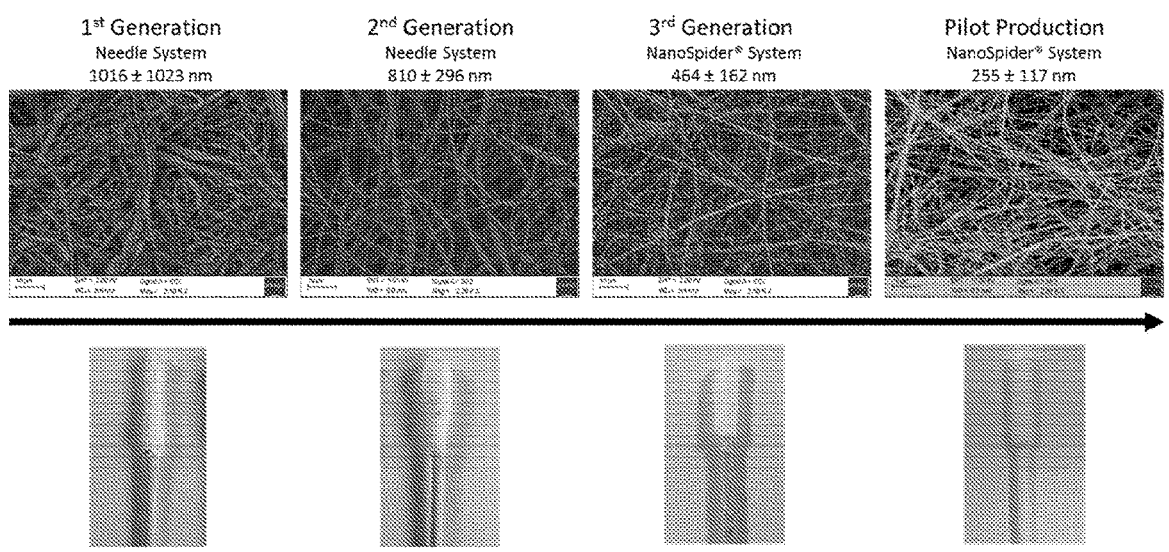
FIG. 2 are photographs showing the refinement of cellulose acetate nanofibers and the corresponding resultant swab produced individually on a needle-based electrospinning setup.

Photomicrographs of representative cellulose acetate nanofiber materials and the resultant material tipped swabs made by such process are shown in FIG. 2. The materials depicted in FIG. 2 show the refinement of cellulose acetate nanofiber (and resultant swab) production whereby the first generations of material were produced individually on a needle-based electrospinning setup while later swab materials were produced on a pilot-scale production system known as the "NanoSpider® system." This system allows production of an order of magnitude of about 10's square feet per day, and can be directly scaled to systems that produce about 10,000's square feet per day.

The cellulose acetate may be co-electrospun with other synthetic polymers to provide enhanced mechanical properties for certain applications. For example, cellulose acetate can be co-electrospun with a small percent (e.g., under 50 wt. %, preferably under 20 wt. %) of polyurethane to result in a material with more flexibility for sample acquisition of rough or complex surfaces in a forensics application. A specific blend specific blend of cellulose acetate co-electrospun with 20 wt. % polyurethane has been formed with complete swab dissolution being observed in the buffer solution. Additional copolymers other than polyurethane that are capable of being co-electrospun with cellulose acetate include, by way of non-limiting example, starch, gluten, collagen, Nylon-6, poly(D,L-Lactic Acid) (PDLLA), polyethylene glycol, polycaprolactone (PCL), Nylon 6/12 and mixtures thereof.

Exemplary surfactants that may be electrospun with cellulose acetate at concentrations below about 50 wt. %, typically below 20 wt. % (e.g., from about 1 to about 20 wt. %) include TRITON™ X-100 nonionic surfactant, TWEEN® 80 nonionic surfactant and the like.

Exemplary buffer solutions include organic electrolyte solutions containing a small molar fractions of ionic liquid for dissolution of cellulose acetate. These solutions have been observed to dissolve raw cellulose in under 3 min [1-Butyl-3-methylimidazolium chloride (BMIMCl)+1,3-dimethyl-2-imidazolidinone (DMI)] and even instantaneously in some cases [1-ethyl-3-methylimidazolium acetate (EMIMAcO)+DMI]. Due to the expense of ionic liquids, the use of guanidinium isothiocyanate (GITC), a chaotropic salt, was investigated to dissolve the swabs. As seen in FIG. 4, a liquid containing a concentration of at least 4M GITC is required for complete dissolution within a relevant time frame (less than 15 minutes at room (20° C.) temperature) in the absence of a primary alcohol (e.g., ethanol). Further, it was confirmed that standard lysis buffers can also dissolve the swabs. Following immersion in the Multi-Sample DNA Lysis Buffer (MagMAX™ kit, Life Technologies) which contains GITC as one component for three minutes, there is near complete dissolution of the swab, as shown in FIG. 5. The standard cotton swabs (right-hand of FIG. 5) show no evident dissolution.

The swabs were tested versus numerous organisms as shown in Table 3 below.

TABLE 3

Summary of swab characterization testing

| Test | Organism |
|---|---|
| Swab recovery testing, bacteria viability (NCCLS document M40-A - Quality Control of Microbial Transport Systems; Approved Standard | Haemophilus influenzae (ATCC 10211) Neisseria gonorrhoeae (ATCC 43069) Streptococcus agalactiae (ATCC 13813) Streptococcus pneumoniae (ATCC 6305) |
| Swab release and recovery testing, virus infectivity via plaque assay | Adenovirus (hAd5) Rhinovirus (hRV1B) Influenza A (PR 8) |
| Sample storage in matrix - bacteria viability, virus infectivity | Haemophilus influenzae (ATCC 10211) Neisseria gonorrhoeae (ATCC 43069) Streptococcus agalactiae (ATCC 13813) Adenovirus (hAd5) Rhinovirus (hRV1B) Influenza A (PR 8) |
| Molecular Detection - Quantitative PCR From swab, and swab & matrix | Haemophilus influenzae (ATCC 10211) Neisseria gonorrhoeae (ATCC 43069) Streptococcus agalactiae (ATCC 13813) Streptococcus pneumoniae (ATCC 6305) |
| Molecular Detection - FDA approved assay | Influenza A (PR 8) Rhinovirus (hRV1B) Adenovirus (hAd5) |
| Release and recovery testing - whole blood | Whole blood cell uptake Whole blood cell DNA recovery (manual) Whole blood cell DNA recovery (Automated) |

TABLE 3-continued

Summary of swab characterization testing

| Test | Organism |
|---|---|
| Release and recovery testing - epithelial cells | Epithelial cell uptake (glass slide) |

The capture and recovery of DNA from dried whole blood for forensics applications has also been investigated. Swabs containing cellulose acetate nanofibers were used (following pre-wetting with approximately 50 µL of DI water) to capture a given number of dried red blood cells from a surface. A Qiagen EZ1 Biostation was then utilized for automated sample recovery and DNA analysis. Results have indicated enhanced recovery as compared to a variety of other swabs when analyzed with the EZ1 Biostation (Qiagen, automated). This is substantially improved as compared to all other tested forensic sampling swabs at 20 µL, as shown in Table 4 below. Performance with 5 µL blood capture and recovery is comparable to the flocked swabs as is shown graphically by FIG. 6.

TABLE 4

Recovery of DNA from human whole blood on various swabs for 5 and 20 µL samples. Presented as total ng recovered and percent recovery. (n = 3 samples per condition).

| Swab | 5 µL Blood | 20 µL Blood |
|---|---|---|
| Blood Control | 2.54 ng recovered | 10.31 ng recovered |
| Popule Swab | 1.22 ng (47.84%) | 4.45 ng (43.19%) |
| Cotton Swab | 1.40 ng (55.05%) | 5.36 ng (52.02%) |
| Rayon Swab | 1.86 ng (73.13%) | 7.23 ng (70.13%) |
| Flocked Swab | 2.05 ng (80.47%) | 6.71 ng (65.11%) |
| Invention (Pre-Wet Swab) | 2.02 ng (79.29%) | 8.46 ng (82.09%) |

The swabs may be produced for collection of sample from a patient or collection of a forensic sample off various surfaces (substrates). It is envisioned that the swabs may be employed for direct integration into a variety of existing or developmental molecular diagnostics devices, or for use with stabilizing buffers or matrices for transport. These stabilizing systems could be traditional Universal Transport Matrix (UTM, virus), Amies Media or Agar, or other gels, liquids, media, or buffers that stabilize either bacterial or viral activity or DNA, RNA, and proteins within the sample. The swabs of course must not be dissolvable with the specific transport media to ensure no dissolution of the swab during transport and to ensure transfer to the appropriate recovery buffer at a lab. The compatibility (no dissolution over 48 hours, and demonstrated DNA/RNA recovery following storage) has been confirmed of the cellulose acetate swabs in accordance with the embodiments disclosed herein with the transport media shown in Table 5 below. In this regard, it is noted that no media or buffers that have been tested which contain no amount of GITC have resulted in any signs of swab dissolution or degradation.

TABLE 5

Transport Media or Matrix Compatibility with Luna's Dissolvable Nanofiber Swabs

| Transport Media or Matrix | Supplier |
|---|---|
| Amies Media | Copan Diagnostics |
| Amies Agar (with and without charcoal) | Copan Diagnostics |
| Universal Transport Matrix | Beckton Dickinson, others |
| HBSS | Various |
| PBS | Various |
| Culture Broths and Inoculum (LB, TSB, etc.) | Various |

For forensic sample use, swabs will either arrive pre-wet or be wetted prior to dry sample acquisition, and then be transferred to a dry storage container (with or without a desiccant) for transport to a diagnostic lab. For use as a filter, the nanofiber membrane will be mounted on a support structure and then removed for dry or wet storage prior to analysis.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope thereof.

What is claimed is:

1. A recovery kit for recovering and facilitating extraction of DNA from a whole blood specimen, wherein the kit comprises:
   a specimen collection swab adapted to collect and retain a sufficient quantity of whole blood to allow DNA extraction therefrom by silica column or functionalized magnetic bead-based DNA isolation techniques, wherein the swab comprises nonwoven cellulose acetate nanofibers having an average diameter from about 100 nm to about 500 nm which are electrospun from a spinning solution comprising 5 to 50% wt/vol of cellulose acetate having a weight average molecular weight of from about 30,000 to about 300,000 g/mol, and
   a dissolution liquid comprising an effective amount of between about 1 to about 10M guanidinium isothiocyanate (GITC) sufficient to dissolve the cellulose acetate nanofibers within about 15 minutes without agitation at about 20° C. and thereby form a DNA extraction solution containing DNA from the whole blood specimen and cellulose acetate from the cellulose acetate nanofibers dissolved therein, wherein
   the specimen collection swab comprises an amount between 1 mg to about 50 mg of the nonwoven cellulose acetate nanofibers such that an amount of dissolved cellulose acetate nanofibers in the DNA extraction solution is insufficient to substantially inhibit DNA yield when extracted by the silica column or functionalized magnetic bead-based DNA isolation techniques.

2. The kit according to claim 1, wherein the dissolution liquid comprises up to about 99 wt. % of a primary alcohol.

3. The kit according to claim 2, wherein the primary alcohol is at least one selected from the group consisting of methanol, ethanol and propanol.

4. The kit according to claim 1, wherein the cellulose acetate nanofibers are formed of electrospun cellulose acetate having between 20 and 50% acetylation.

5. A method for recovering and facilitating extraction of DNA from a whole blood specimen by silica column or functionalized magnetic bead-based DNA isolation techniques, wherein the method comprises the steps of:

(a) providing the recovery kit according to claim 1;
(b) obtaining a whole blood specimen by bringing whole blood into contact with the specimen collection swab of the recovery kit such that the whole blood specimen is collected by the cellulose acetate nanofibers;
(c) placing the specimen collection swab of the recovery kit with the whole blood specimen collected by the cellulose acetate nanofibers thereof into the dissolution liquid of the recovery kit; and
(d) allowing the cellulose acetate nanofibers to dissolve in the dissolution liquid to thereby form the DNA extraction solution containing the DNA from the whole blood specimen and the dissolved cellulose acetate in an amount insufficient to substantially inhibit DNA yield when extracted by the silica column or functionalized magnetic bead-based DNA isolation techniques.

6. The method according to claim 5, wherein the cellulose acetate nanofibers are formed of cellulose acetate having between 20 and 50% acetylation.

7. The method according to claim 5, wherein step (a) comprises (a1) bringing the nanofibers of the swab into contact with a whole blood specimen so that the whole blood specimen is captured by the nanofibers of the swab.

8. The kit according to claim 5, wherein the dissolution liquid comprises up to about 99 wt. % of a primary alcohol.

9. The kit according to claim 8, wherein the primary alcohol is at least one selected from the group consisting of methanol, ethanol and propanol.

10. The method according to claim 5, wherein step (b) comprises immersing the biological specimen recovery material in the dissolution liquid to dissolve the cellulose acetate nanofibers thereof.

* * * * *